United States Patent
Roessl et al.

(10) Patent No.: US 10,223,815 B2
(45) Date of Patent: Mar. 5, 2019

(54) ITERATIVE RECONSTRUCTION METHOD FOR SPECTRAL, PHASE-CONTRAST IMAGING

(71) Applicant: KONINKLIJKE PHILIPS N.V., Eindhoven (NL)

(72) Inventors: Ewald Roessl, Ellerau (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 104 days.

(21) Appl. No.: 15/326,506

(22) PCT Filed: Jul. 16, 2015

(86) PCT No.: PCT/EP2015/066222
§ 371 (c)(1),
(2) Date: Jan. 16, 2017

(87) PCT Pub. No.: WO2016/008956
PCT Pub. Date: Jan. 21, 2016

(65) Prior Publication Data
US 2017/0206682 A1    Jul. 20, 2017

(30) Foreign Application Priority Data

Jul. 17, 2014 (EP) .................... 14177420

(51) Int. Cl.
*G06K 9/00* (2006.01)
*G06T 11/00* (2006.01)
(Continued)

(52) U.S. Cl.
CPC ............ *G06T 11/008* (2013.01); *A61B 6/032* (2013.01); *A61B 6/484* (2013.01); *A61B 6/5205* (2013.01);
(Continued)

(58) Field of Classification Search
CPC ....... A61B 6/032; A61B 5/055; A61B 6/5258; G06T 2207/10081; G06F 19/00
(Continued)

(56) References Cited

U.S. PATENT DOCUMENTS 4,342,916 A    8/1982  Jatteau
9,220,469 B2*  12/2015  Jin ....................... A61B 6/4241
(Continued)

FOREIGN PATENT DOCUMENTS

WO    2010/042629    4/2010
WO    2011/011014    1/2011
(Continued)

OTHER PUBLICATIONS

Epple et al, "Unwrapping differential X-ray phase contrast images through phase estimation from multiple energy data" Optics Express, Dec. 2, 2013, vol. 21, No. 24.
(Continued)

*Primary Examiner* — Charlotte M Baker
(74) *Attorney, Agent, or Firm* — Larry Liberchuk

(57) ABSTRACT

A system and related method for X-ray phase contrast imaging. A signal model is fitted to interferometric measurment data. The fitting operation yields a Compton cross section and a photo-electric image. A pro-portionality between the Compton cross section and electron-density is used to achieve a reduction of the number of fitting variables. The Compton image may be taken, up to a constant, as a phase contrast images.

13 Claims, 3 Drawing Sheets

(51) Int. Cl.
*A61B 6/03* (2006.01)
*A61B 6/00* (2006.01)
*G01N 23/20* (2018.01)

(52) U.S. Cl.
CPC ...... *G01N 23/20075* (2013.01); *G06T 11/006* (2013.01)

(58) Field of Classification Search
USPC ................................ 382/131; 378/5, 901, 19
See application file for complete search history.

(56) References Cited

U.S. PATENT DOCUMENTS

| | | | |
|---|---|---|---|
| 9,613,441 | B2 | 4/2017 | Koehler |
| 9,842,414 | B2 | 12/2017 | Koehler |
| 2002/0044628 | A1 | 4/2002 | Hussein |
| 2008/0128631 | A1 | 6/2008 | Suhami |
| 2012/0236987 | A1* | 9/2012 | Ruimi ................. A61B 6/032 378/19 |
| 2012/0314834 | A1 | 12/2012 | Yao |
| 2013/0010927 | A1 | 1/2013 | Seppi |
| 2013/0032715 | A1 | 2/2013 | Zhu |
| 2014/0079184 | A1 | 3/2014 | Das |

FOREIGN PATENT DOCUMENTS

| | | |
|---|---|---|
| WO | 2011/145040 | 11/2011 |
| WO | 2012/029039 | 3/2012 |
| WO | 2014/000996 | 1/2014 |

OTHER PUBLICATIONS

Pfeiffer et al in "Phase retrieval and differential phase-contrast imaging with low-brilliance X-ray sources," Nature Phys. Lett. 2, 258-261 (2006).

Ritter et al. "Simultaneous maximum-likelihood reconstruction for x-ray grating based phase-contrast tomography avoiding intermediate phase retrieval", Jul. 30, 2013.

Masuji, et al., "A study on electron density imaging using the Compton scattered X-ray CT technique", Nuclear Instruments and Methods in Physics Research A 652 (2011) 620-624.

Cooper "Compton Scattering and the Study of Electron Momentum Density Distributions", Radiat. Phys. Chem., vol. 50, No. 1, 1997.

Koehler, et al., "Iterative reconstruction for differential phase contrast imaging using spherically symmetric basis functions", Med. Phys. 38 (8), Aug. 2011.

Wu, et a.., "Phase retrieval from one single phase contrast x-ray image", Optics Express, vol. 17, No. 13, Jun. 22, 2009.

Iwamoto, S-I. et al., "Basic Study for the Direct Measurement of Electron Density", NII-Electronic Library Service, Faculty of Health Sciences, Butsuryo College of Osaka, Nov. 28, 2013, pp. 9-18.

* cited by examiner

ITERATIVE RECONSTRUCTION METHOD FOR SPECTRAL, PHASE-CONTRAST IMAGING

CROSS REFERENCE TO RELATED APPLICATIONS

This application is the U.S. National Phase application under 35 U.S.C. § 371 of International Application No. PCT/EP2015/066222, filed Jul. 16, 2015, published as WO2016/008956 on Jan. 21, 2016, which claims the benefit of European Patent Application Number 14177420.8 filed Jul. 17, 2014. These applications are hereby incorporated by reference herein.

FIELD OF THE INVENTION

The invention relates to signal processing system, to a signal processing method, to a computer program element and to a computer readable medium.

BACKGROUND OF THE INVENTION

It has been observed that phase-contrast computed tomography (CT) imagery and CT Compton cross-section absorption imagery (obtained from a spectral material decomposition) are inflicted by relatively high image noise levels in the high frequency range for phase-contrast imaging and the low frequency range for spectral imaging, respectively. What is more, spectral material decomposition may require special detector hardware, in particular photon-counting and/or energy resolving detectors, which may be expensive to procure.

SUMMARY OF THE INVENTION

There may therefore be a need for alternative image signal processing methods and related systems to address at least some of the above mentioned disadvantages.

The object of the present invention is solved by the subject matter of the independent claims where further embodiments are incorporated in the dependent claims.

It should be noted that the following described aspect of the invention equally apply to the signal processing method, to the computer program element and to the computer readable medium.

According to a first aspect of the invention, there is provided a signal processing system comprising:

an input port for receiving measurement data detected at an X-ray sensitive detector of an interferometric X-ray imaging system, after passage of an X-ray beam through a sample;

a model initializer configured to include said data into a signal model;

a model fitting module configured to perform, for a plurality of detector pixels, a fitting operation to fit parameters of said signal model to the measurement data wherein the signal model includes parameters that represent attenuation of the X-ray beam, wherein at least one of the parameters accounts for photo-electric effect interaction and at least one of the parameters accounts for Compton scattering, wherein the Compton scattering parameter is a surrogate for the electron density in said sample, wherein the signal model includes a term that models, as a function of the Compton scattering, a modulation of a phase change induced by the object;

an output port configured to output at least some of the fitted parameters as a photo-electric absorption image or as a Compton scattering image, respectively.

In other words, we propose to use the interferometric imaging setup (normally used for dedicated phase contrast imaging) to perform, based on the interferometric measurement data, a "simulated" dual energy spectral imaging to obtain at least one of the photo-electric absorption image (also called photo-electric cross-section image) and/or a Compton scattering image (also called Compton cross section image). In the fitting operation as proposed herein we use Compton scattering as a surrogate or substitute for electron density in the model and thereby harness the fact that the two quantities are physically related. In yet other words, in the proposed signal model, the Compton scattering contribution takes over the role of the electron density contribution. This judicious substitution (that is, Compton scattering for electron density) allows cutting down the number of parameters to solve for and this parameter reduction in turn yields a noise reduction in the output data. The phase contrast image data may then be identified with the Compton scattering image, up to a physical constant independent of the object to be imaged.

In other words and according to one embodiment, the Compton scattering image provides information in relation to the electron density and/or a phase contrast image. The Compton scattering image is indicative of the electron density, that is, of an image of the electron density in the sample and hence of the phase contrast image, too.

The phase contrast information in the measurement data is accounted for by having, according to one embodiment, the signal model include a term that represents a modulation caused by a phase-shift induced by the sample and wherein said term includes a spatial derivative of the Compton scattering variable.

According to one embodiment, the system includes a reconstructor configured to reconstruct for a volumetric voxel image, that is, for a cross-sectional slice image based on at least some (that is, one or more) of the fitted parameters.

According to one embodiment, the fitting operation includes approximating the spatial derivative of the Compton scattering parameter through one or more finite differences of the respective fitted Compton scattering variables associated with neighboring detector pixels or pixel readings. Approximation by finite differences from neighboring pixels (for any given pixel) allows forming projection images. If a volumetric "slice" image of the Compton (or energy density or phase contrast) or photo-electric cross-section is to be formed, the approximation via neighborhoods may be circumvented by analytically forming the derivative of suitable basis functions associated with respective voxels.

According to one embodiment, the measurement data is acquired along a single projection direction or is acquired from a plurality of projection directions.

According to one embodiment, the detector is of the energy integrating type, in particular is not of the photon counting or energy resolving type.

The proposed system may be used with benefit for or in 2D projection imaging systems or computer tomography (CT) scanner systems. The present invention allows for useful application in a clinical environment such as a hospital. More specifically, the present invention is very suitable for the medical examination of patients. In addition, the presentation invention allows for useful application in an industrial environment. More specifically, the present invention is very suitable for application in non-destructive testing (e.g. analysis as to composition, structure and/or qualities of biological as well non-biological samples) as well as security scanning (e.g. scanning of luggage on airports).

In sum, the proposed system advantageously circumvents the generation of an entire dataset, namely the line integral of electron density. This has a further advantage in that the eventual phase contrast images and Compton images from spectral CT have less noise. It furthermore advantageously enables decomposing phase contrast CT data without the need for a spectral detector.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
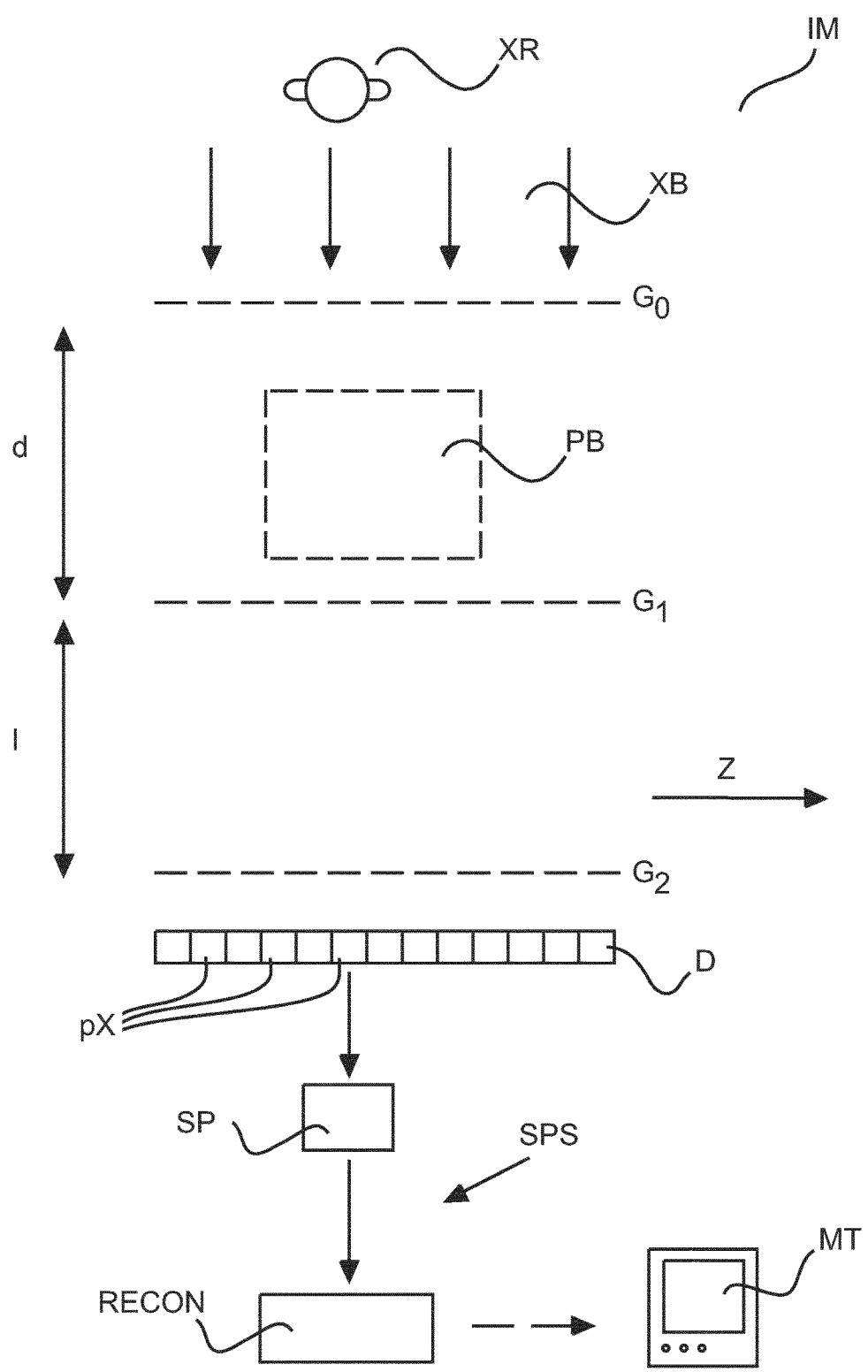
FIG. 1 shows an imaging arrangement for differential phase contrast imaging.

FIG. 1 shows basic components of an imaging system IM with phase contrast imaging capabilities, in particular differential phase contrast imaging (DPCI).

There is an X-ray source XR for generating X-ray radiation waves XB that, after passage through a specimen PB in an examination region, are detectable by detector pixels px of a detector D. An object support (not shown) such as a couch supports the specimen PB (such as a patient or an inanimate object, e.g. an item of baggage, etc) in the examination region.

The imaging system IM is either a CT scanner for 3D imaging or may also be a simpler planar projection imager apparatus such as of the C-arm type. At least the x-ray source is mounted on a rotatable gantry to project the x-ray waves through the patient at any one or a plurality of desired projection directions.

The phase contrast imaging capability is achieved by an interferometer arranged between the X-ray source XR and the radiation sensitive detector D.

The interferometer (which in one non-limiting embodiment is of the Talbot type or of the Talbot-Lau type) includes two $G_1$, $G_2$ (Talbot type) or more, preferably, three gratings $G_0$, $G_1$ and $G_2$ (Talbot-Lau type). The first attenuation grating $G_0$ at the X-ray source side has a period $p_0$ to match and cause spatial coherence of the X-ray radiation wave front emitted at the X-ray source XR.

An phase grating $G_1$ (having period $p_1$) is placed at distance d from the X-ray source and causes an interference pattern with period $p_2$ further downstream. Said interference pattern can be detected by detector D. Employing such phase grating, in addition the generation of image data deriving from de-coherent X-ray small angle scattering is enabled, the latter type of imaging also being referred to as "dark field imaging". Now, when a sample PB (to be imaged) is introduced in the examination region between the X-ray source and the detector, the phase of the interference pattern is then shifted. This interference pattern shift $\Delta\varphi$ (as has been reported elsewhere, for instance in F M Epple et al, Unwrapping differential X-ray phase contrast images through phase estimation from multiple energy data, OPTICS EXPRESS, 2 Dec. 2013, vol 21, No 24) is proportional to the gradient of the phase shift $\Delta\Phi$ due to the accumulated refraction along respective paths through the sample PB (hence the name DCPI). In other words, if one were then to measure the phase change of the interference, this would allow to extract the shift (or gradient) of the phase shift that is caused by refraction in the sample PB.

Unfortunately the phase shift of the interference pattern is typically too small to be directly spatially resolved. The resolution powers of most X-ray detectors would not allow this. Therefore in order to "sample" this interference pattern phase shift, a second attenuation rating $G_2$ with the same period $p_2$ as the interference pattern is placed at a distance l from grating $G_1$. The actual extraction of the interference pattern phase shift (and hence that of the phase gradient caused by the sample PB) can be achieved in a number of different ways according to different embodiments that are all envisaged herein.

In some embodiments a relative motion between the detector D and at least one of the gratings is required for differential phase extraction. This can be achieved in one embodiment by "phase stepping" where an actuator is used to laterally move for instance, analyzer grating $G_2$ across different, discrete grating positions and then measure at each grating position the intensity at each pixel px. "Lateral" motion means herein along z direction (see FIG. 1), that is, motion in a direction perpendicular to the propagation direction of the wave XB and the "trench" directions of the gratings. The phase-stepping approach has been described by F. Pfeiffer et al in "Phase retrieval and differential phase-contrast imaging with low-brilliance X-ray sources," Nature Phys. Lett. 2, 258-261 (2006).

But that is not to say that phase stepping is the only embodiment, as in other embodiments the motion may be that of the specimen itself or it may be a scanning motion of the X-ray detector (with at least some of the gratings G1 and or G2 mounted therein) which constitutes the required motion. What matters herein, is to capture a signal that includes the amount of refraction induced by the presence of the specimen PB in the examination region.

In general, the intensity I at each pixel will be found to oscillate (in general in a sinusoidal fashion). In other words, each pixel records a time series of different intensities (at the respective pixel) as a function of time (or better as a function of the different grating positions) during motion of the analyzer grating G2.

The oscillating intensity signal I at each pixel px "encodes" amongst other quantities the overall attenuation (that is partly absorption and partly scattering) and the desired phase shift of the interference pattern.

If the x-ray imaging system is of the CT scanner type, the intensity signals for each pixel will be recorded from different projection directions. If the imaging system is a 2D planar projection imager, the intensities are acquired from a single projection direction for a desired projection image. The collection of intensities as recoded per pixels (and in CT per projection direction) will be referred to herein as interferometric projection raw data.

The interferometric projection raw data is forwarded to a signal processing system SPS or backend that includes a signal processing module SP and, in the CT embodiment, a reconstructor module RECON to reconstruct the intensity signals from the plurality of directions into a cross sectional image of the specimen.

The signal processing system SPS includes a signal processing module SP that operates to spectrally decompose, in a new manner to be explained in more detail below, the interferometric projection raw data into one or more or all of the following: a Compton scattering cross-sectional or projection image, a photo-electric absorption cross-sectional or projection image or an electron density image cross-sectional or projection image or a cross-sectional or projection dark field image.

Suitable visualization modules can then operate to visualize the respective cross-sectional or projection images on a monitor or display MT. The signal processing system with or without the re-constructor RECON and/or the visualization module and other control modules may be run on a general purpose computer that serves as an operator console (not shown) for the imaging arrangement. The console is communicatively coupled to an input device such as a keyboard and/or mouse and to the monitor MT.

Counterintuitively to what has been done previously, we propose herein to use the interferometric imaging set up to perform a spectral decomposition to obtain in particular the Compton or photo-electric or electron density data. The Compton image data as determined herein is, up to constant, identical to the phase contrast image. Unlike previous approaches, no dual energy x-ray source is required and also the x-ray detector can be of the energy integrating type. In particular, no energy resolving or photon counting detector is required herein.

The approach as proposed herein allows obviating high frequency image noise that usually inflicts dual energy decomposition imagery if processed in the usual manner and low frequency image noise that usually inflicts the phase-contrast imagery if processed in the usual manner. More particularly, It is known that material decomposition in dual-energy imaging or photon-counting, energy discriminating computed-tomography, spectral CT, produces typically very noisy basis material images (high frequency noise) together with highly correlated noise behavior with respect to the photo-electric component). Hence, for the commonly used physical basis of photo-electric and Compton effects, this means that the electron density image derived from the Compton-material-basis image $a_{Co}$, $(\vec{r})$ will feature high levels of high frequency noise anti-correlated with the high-frequency noise in the Photo-electric image.

$$\mu(E_D) = \mu_{Ph}(E_D) a_{Ph}(\vec{r}) + \mu_{Co}(E_D) a_{Co}(\vec{r})$$

In computed tomography, in view of the filtration step that amplifies high frequencies, the electron density image so obtained will also have the peak of the noise power in the high frequency end of the spectrum.

In conventional gratings-based, differential phase-contrast imaging, the electron density can be assessed because the deviation of the x-rays from their forward propagation direction measured by the fringe phase $\Phi$ is proportional to the gradients of the line-integrals of the electron-density perpendicular to the gratings trenches (z in our notation):

$$\Phi\left(E, \frac{\partial A_e}{\partial z}\right) = \alpha(E) \frac{\partial}{\partial z} \int \rho_e(\vec{r}(s)) ds = \alpha(E) \frac{\partial A_e}{\partial z},$$

where $\alpha(E)$ is a proportionality constant depending on energy. As differential phase-contrast imaging is sensitive to the gradient of electron density, the conventional reconstruction from phase data involves a Hilbert-Filter instead of a ramp filter (used with traditional absorption based filtered back-projection) with a relative high (and for CT atypically) low-frequency noise in the so-obtained electron density images.

In other words, both, conventional dual spectral imaging and conventional phase-contrast CT imaging generate electron-density images with either unwanted high-frequency noise or low frequency noise.

It is proposed herein then to use the physical insight, that both, Compton effect and refraction are determined by the same physical quantity (namely the electron density) to reduce noise in imaging results. We propose to consolidate this physical insight into a common forward signal model (see eq (3) below) and to use same to obtain the desired Compton, photo-electric, electron density, or dark field image data.

A spectral forward model for the intensity measurements to be expected during differential, gratings-based phase-stepping can be written:

$$I_n\left(A_{Ph}, A_{Co}, \frac{\partial A_e}{\partial z}, \Omega\right) = \tag{1}$$
$$\int \tilde{\Phi}(E) S(E) e^{-\mu_{Ph}(E) A_{Ph} - \mu_{Co}(E) A_{Co}} \left(1 + V(E) e^{-\Omega f_{DC}(E)} F\left(\frac{2\pi n}{n} + \alpha(E) \frac{\partial A_e}{\partial z}\right)\right) dE$$

In Eq. (1), $\tilde{\Phi}(E)$, $S(E)$, $\mu_{Ph}(E)$, $V(E)$, $f_{DC}(E)$, $\alpha(E)$ describe the source spectrum, the detector sensitivity function of the spectral measurement and the energy dependence of the attenuation of the photo-electric effect and the Compton effect, the visibility of the interferometer, the scattering and the refraction of x-rays, respectively. The functional dependences of these parameters are known or can be readily established. $S(E)=E$ or $=1$ for photon counting detectors or energy integrating detectors, respectively. For energy-selective photon-counting detectors for a single frame, several bin-sensitivity functions $S_m(E)$ will replace the single $S(E)$ for the detectors with one reading per frame. Preferably the detector is of the energy integrating type.

$A_{Ph}$, $A_{Co}$, $$\frac{\partial A_e}{\partial z},$$

$\Omega$ denote the quantities of interest, namely the line integrals (for a given projection direction or path from the X-ray source to the respective detector pixel) of the photo-electric absorption, the Compton scattering, the gradient of the electron density change in z-direction, and of the scattering power of the specimen (related to the dark field image).

The function $F(\ldots)$ describes the specific modulation of the x-ray intensity measured at the detector upon phase stepping, and can be approximated by a trigonometric function (eg, a sinusoidal function). Putting our insight from above in the form of an equation, we can write:

$$\rho_e(\vec{r}) = c a_{Co}(\vec{r}) \text{ or } A_e = c A_{Co}, \tag{2}$$

in which case (1) reduces to:

$$I_n(A_{Ph}, A_{Co}, \Omega) = \tag{3}$$
$$\int \tilde{\Phi}(E) S(E) e^{-\mu_{Ph}(E) A_{Ph} - \mu_{Co}(E) A_{Co}} \left(1 + V(E) e^{-\Omega f_{DC}(E)} F\left(\frac{2\pi n}{N} + c\alpha(E) \frac{\partial A_{Co}}{\partial z}\right)\right) dE$$

In particular, the term F( ) that models the modulation of the phase change induced by the object now includes a Compton absorption line integral in place of the electron density line integral. In other words, the Compton information now serves as a surrogate or substitute for the electron density information. The simplification in (3) as compared to (1) can now be exploited in various ways. We give two embodiments in the following, one related to computed tomography, the other to projection imaging.

Figure 2:
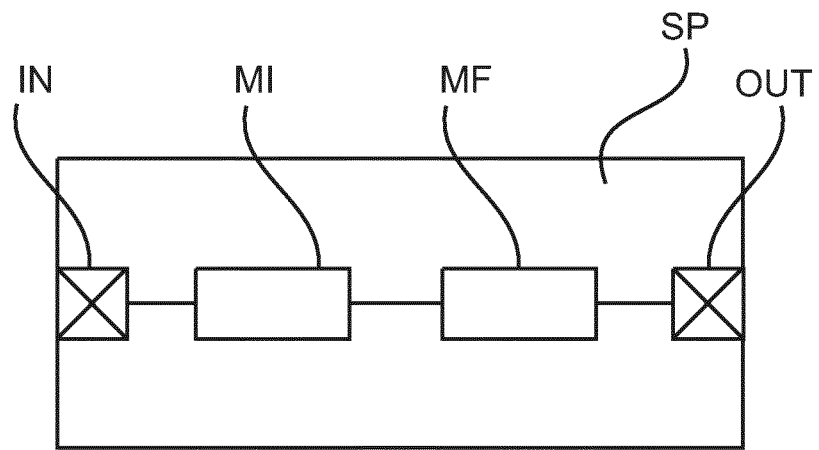
FIG. 2 shows a component of the arrangement in FIG. 1.

With reference to FIG. 2, the dual spectral processing system as proposed herein includes an input port IN and an output port OUT, a model initializer MI and a model fitter MF. Broadly, the interferometric projection raw data (in other words the varying intensities per pixel and (in CT) per projection direction) are received at input port IN. Model initializer MI then includes the so received data into a functional description of the model as per eq (3) or mathematical equivalents thereof. More particularly the initialization includes equating the respective intensities I with the right hand side of the functional eq (3). Initialization also includes including the values for $\bar{\Phi}$, S, V, α, $f_{DC}$, $\mu_{Ph}$ and $\mu_{Co}$ into the right hand side of eq (3). The later mentioned quantities can be obtained by calibration imaging and the attenuation coefficients are in general known and their energy dependency can be obtained from look-tables or can be interpolated therefrom. Using suitable numerical techniques for instance least squares or maximum-likelihood (ML) methods, the desired image data parameters, that is, the line integrals per pixel/projection direction $A_{Ph}$, $A_{Co}$ and Ω are then fitted to the received interferometric measurement data. At the conclusion of the fitting operation, the respective line integrals can be output as a 2D projection images or the respective projection images for each direction can be forwarded to the re-constructor RECON to reconstruct for the cross sectional slice image of the specimen. In particular, the Compton projection image or the slice reconstructed from the respective line integrals can be output (possibly after suitable conversion as per equation 2) as an image of the electron density.

Figure 3:
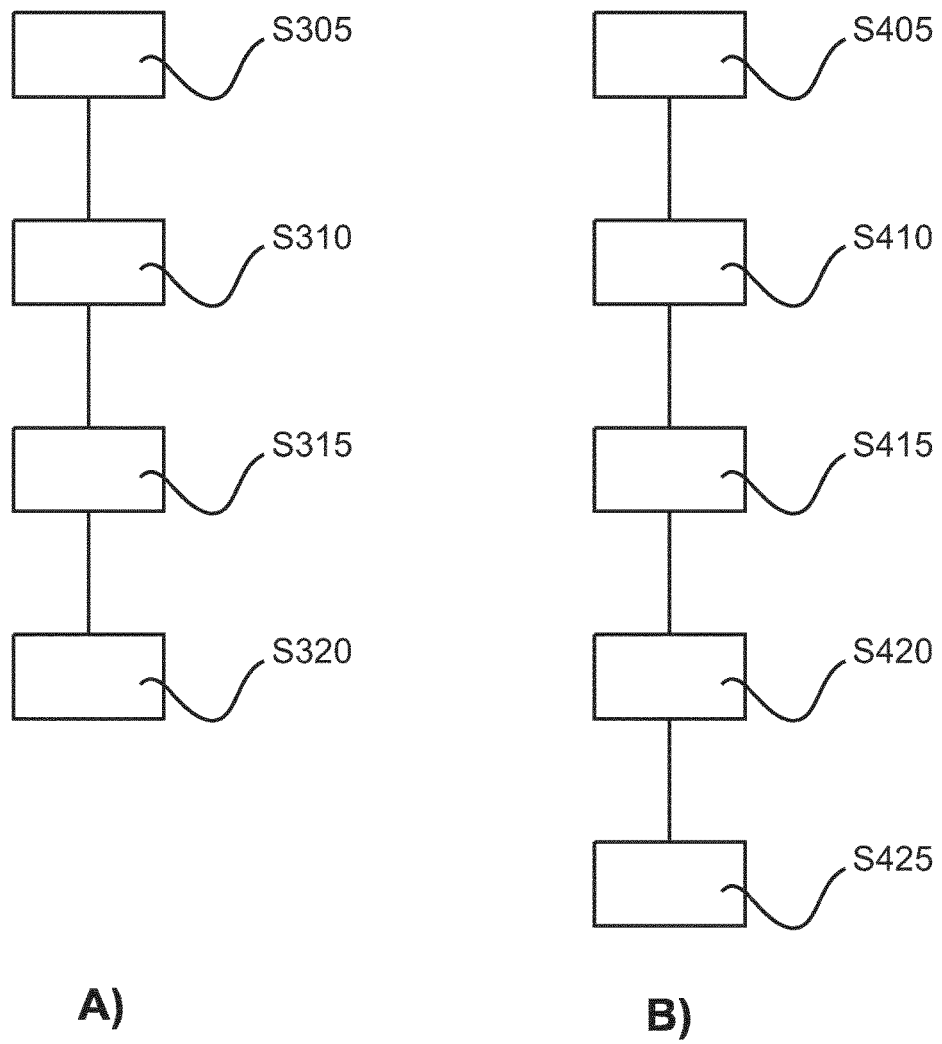
FIG. 3 shows flow charts of signal processing methods according to different embodiments.

Reference is now made to the flow charts in FIG. 3 where the signal processing as proposed herein will be explained in more detail. Flow chart A) details the projection imaging embodiment and flow chart B) details the CT tomography embodiment.

Turning first to projection imaging as per flow chart A), at step S305 the interferometric projection raw data is received.

At step S310 the interferometric projection raw data is included in the forward model as per equation 3 or mathematical equivalents thereof At step S315 the model as per eq (3) or mathematical equivalent thereof is fitted to the interferometric projection raw data, that is, to the respective intensities recorded at the respective pixels. More particularly for each pixel and intensities from the time series of intensities a respective eq (3) is solved for the unknown line integrals $A_{Ph}$, $A_{Co}$ and Ω.

Unfortunately, on the projection data plane, $A_{Co}$, and $$\frac{\partial A_{Co}}{\partial z}$$

cannot be related directly. To tackle this, we propose to use the neighborhood (in z) to relate the measured fringe phase (that is, the intensities detected by pixels in the neighborhood of the current pixel of interest) to finite differences of the Compton line-integral $A_{Co}$. In other words, the derivate is approximated by computing finite differences across a neighborhood over the $A_{Co}$'s of neighboring pixels.

The fitting operation may be achieved by suitable numerical/optimization techniques the selection of which being largely determined by the number of intensity measurements I available per detector pixel. If there are as many measurements I as there are parameters to be fitted (eq (3) asks for 3 parameters to be fitted) we can solve a system of simultaneous equations. If there are more than three measurements I, the system is over-determined. In this case an objective function is set up based in eq (3). For instance, the objective function may be one of least-squares for the residuals or a maxim-likelihood function based on a suitable noise model (eg Gaussian) for the measurements. Suitable optimization algorithms may then be used to maximize or minimize the objective function to obtain the desired line integrals.

At step S320 the solved for line integrals are then output as the respective photo-electric and/or Compton and/or dark field image. In particular, the Compton image can be output as the electron density image after possible conversion as per equation 2.

Turning now to the CT embodiment the proposed Compton versus electron density substitution in the forward model as per eq (3) can be used with particular benefit, in particular because no evaluation of the neighborhood pixels is required as in the projection imaging embodiment of flow chart 3A). As applied to computed tomography, is the proposed method makes it possible to eliminate an entire image data set (the electron density images that is) from the quantities to be determined via the relation between electron density and Compton cross section.

Referring now to the flow chart 3B), at step S405 the interferometric projection raw data is received.

At step S410 the model as per eq (3) is initialized as explained earlier at step S315.

At step S415 eq (3) is solved for each projection direction and pixel into the line integrals as before at step S315, however, this time no approximation of the derivative (in z direction) of the Compton line integral $A_{Co}$ in a neighborhood is required but may be formed instead analytically from basis functions associated with voxels in image space as will be explained in more detail below at reconstruction step S425.

As step S420 the computed line integrals are output for further processing such as reconstruction in the next step.

At step S425 the line integrals for each projection direction are then reconstructed in a conventional filtered back projection or preferably in an iterative reconstruction into a cross sectional voxel image. An iterative reconstruction is preferable because it allows directly basing the reconstruction on the model as per (3).

In iterative reconstruction an initial estimate for the cross sectional image to be reconstructed is used. Voxels in image space that correspond to the estimated cross section are then forwarded projected (by summing, in the conventional manner, over the respective voxels for each projection direction of interest) to form estimated line integrals. The estimated line integrals are then compared with the fitted line integrals as per step S415. If there is a discrepancy, a suitable updating is applied to update the initial estimate for the cross sectional image in image space. This forward projecting and updating are then repeated in an iteration loop until a convergence at a satisfactory level is established. After convergence is established or after abortion of iteration, the current estimate for the cross sectional image is then output as the final result.

According to one embodiment, the iterative reconstruction scheme as sketched above uses the concept of building up the estimated cross sectional images in "image space" (as opposed to the" projection space" in which the line integrals as defined) by means of a (linear) combination of basis functions ("blobs"), e.g. the 2D Kaiser-Bessel functions or other suitable function families. Details of this can be found in T. Koehler et al, "Iterative reconstruction for differential phase contrast imaging", pp 4542-4545, Med. Phys. 38 (8), August 2011. See for instance p 4543, left column, FIG. 1. This text is incorporated herein by reference in its entirety.

The numerical advantage mentioned earlier of not having to approximate derivatives flows from this basis function representation in image space. In other words, each of the estimated images is represented by a superposition of basis functions located at each voxel of the reconstructed/estimated image, each basis function multiplied by some coefficient. The derivative of the $A_{C_0}$ can then be computed analytically (not merely approximately) as a linear combination of the analytical derivatives of the basis functions in the respective projection direction. Because the approximation of the derivatives can be obviated so can be a possible source of noise that may otherwise inflict the reconstruction results.

As can be seen from above, in computed tomography the simplification as per model (3) comes immediately to bear. Instead of modeling the images for the Compton cross sections $a_{C_0}(\vec{r})$ and the electron density $\rho_e(\vec{r})$ separately, only one image needs to be considered, e.g. during an iterative reconstruction technique based on model (3). The elimination of fitting a variable separately to the electron density line integral will lead to improved noise performance as compared to a technique based on model (1). It will be most beneficial if the reconstruction is based directly on Eq. (3). This type of reconstruction does not do dedicated phase retrieval (that is a dedicated Fourier analysis per pixel a proposed elsewhere, see for instance eqs (1$a$), (1$b$) in the Epple or see the Pfeiffer paper) so computation time can be saved.

We emphasize that the identification (up to a constant) of electron density and Compton cross section permits to decompose the measured interferometric (CT) data (obtained for instance by phase-stepping or otherwise) into basis materials (photo/Compton) without the need for a spectral detector (that is, a photon counting and/or energy resolving one).

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging system, comprising:
    an X-ray source for generating X-ray radiation waves;
    an X-ray detector, including a plurality of detector pixels, for detecting the X-ray radiation waves after passing through a specimen and providing measurement data; and
    a signal processing system for processing the measurement data, the signal processing system comprising:

an input port for receiving the measurement data;

a model initializer configured to include the measurement data into a signal model;

a model fitting module configured to perform, for the plurality of detector pixels, a fitting operation to fit parameters of the signal model to the measurement data, wherein the signal model includes parameters that represent attenuation of the X-ray radiation waves, wherein at least one of the parameters accounts for photo-electric effect absorption or Compton scattering, wherein the Compton scattering parameter is a surrogate for the electron density in the specimen, wherein the signal model includes a term that models, as a function of the Compton scattering, a modulation of a phase change induced by the specimen;

an output port configured to output at least some of the fitted parameters as a photo-electric absorption image or a Compton scattering image.

2. The imaging system of claim 1, wherein the Compton scattering image provides information in relation to the electron density and/or a phase contrast image.

3. The imaging system of claim 1, wherein said term includes a spatial derivative of the Compton scattering parameter.

4. The imaging system of claim 1, including a reconstructor configured to reconstruct for a cross-sectional slice image based on at least some of the fitted parameters.

5. The imaging system of claim 1, wherein the fitting operation includes approximating the spatial derivative through differences of the fitted Compton parameter for neighboring detector pixel readings.

6. The imaging system of claim 1, wherein the fitting operation includes analytically forming the derivate based on derivatives of basis functions associated with respective voxels.

7. The imaging system of claim 1, wherein the measurement data is acquired along a single projection direction or is acquired from a plurality of projection directions.

8. The imaging system of claim 1, wherein the X-ray detector is of the energy integrating type.

9. The imaging system of claim 1, wherein the imaging system is a 2D projection imager or a computed tomography scanner.

10. A method for imaging a specimen, comprising:

generating X-ray radiation waves by an X-ray source;

detecting the X-ray radiation waves after passing through the specimen and providing measurement data by an X-ray detector that includes a plurality of detector pixels; and processing the measurement data by a signal processing system, the processing comprising:

receiving the measurement data;

including the measurement data into a signal model;

for the plurality of detector pixels, fitting parameters of the signal model to the measurement data, wherein the signal model includes parameters that represent attenuation of the X-ray beam, wherein one of the parameters accounts for photo-electric absorption or Compton scattering, wherein the Compton scattering parameter is a surrogate for the electron density in the specimen, wherein the signal model includes a term that models, as a function of the Compton scattering, a modulation of a phase change induced by the object;

outputting at least some of the fitted parameters as a photo-electric absorption image or a Compton scattering image.

11. The method of claim 10, comprising:

reconstructing for a cross-sectional slice image based on at least one or more of the fitted parameters.

12. The method of claim 10, wherein the Compton scattering image is indicative of an image of the electron density and/or of a phase contrast image.

13. A non-transitory computer-readable medium having one or more executable instructions stored thereon, which when executed by a processor, cause the processor to perform a method for imaging a specimen, the method comprising:

generating X-ray radiation waves by an X-ray source;

detecting the X-ray radiation waves after passing through the specimen and providing measurement data by an X-ray detector that includes a plurality of detector pixels; and processing the measurement data by a signal processing system, the processing comprising:

receiving the measurement data;

including the measurement data into a signal model;

for the plurality of detector pixels, fitting parameters of the signal model to the measurement data, wherein the signal model includes parameters that represent attenuation of the X-ray beam, wherein one of the parameters accounts for photo-electric absorption or Compton scattering, wherein the Compton scattering parameter is a surrogate for the electron density in the specimen, wherein the signal model includes a term that models, as a function of the Compton scattering, a modulation of a phase change induced by the object;

outputting at least some of the fitted parameters as a photo-electric absorption image or a Compton scattering image.

* * * * *